(12) United States Patent
Steinle et al.

(10) Patent No.: US 10,905,517 B2
(45) Date of Patent: Feb. 2, 2021

(54) IMAGE-BASED CONTROLLING METHOD FOR MEDICAL APPARATUSES

(75) Inventors: Wolfgang Steinle, Munich (DE); Nils Frielinghaus, Heimstetten (DE); Christoffer Hamilton, Munich (DE)

(73) Assignee: BRAINLAB AG, Munich (DE)

( * ) Notice: Subject to any disclaimer, the term of this patent is extended or adjusted under 35 U.S.C. 154(b) by 947 days.

(21) Appl. No.: 12/418,698

(22) Filed: Apr. 6, 2009

(65) Prior Publication Data

US 2009/0259960 A1  Oct. 15, 2009

Related U.S. Application Data

(60) Provisional application No. 61/045,313, filed on Apr. 16, 2008.

(30) Foreign Application Priority Data

Apr. 9, 2008  (EP) ..................... 08154245

(51) Int. Cl.

| G06F 3/01 | (2006.01) |
|---|---|
| A61B 90/00 | (2016.01) |
| A61B 6/00 | (2006.01) |
| A61B 17/00 | (2006.01) |
| A61B 34/00 | (2016.01) |
| A61B 34/10 | (2016.01) |

(52) U.S. Cl.
CPC .............. *A61B 90/36* (2016.02); *A61B 6/469* (2013.01); *G06F 3/013* (2013.01); *A61B 34/10* (2016.02); *A61B 34/25* (2016.02); *A61B 2017/00199* (2013.01); *A61B 2017/00207* (2013.01); *A61B 2090/365* (2016.02); *A61B 2090/378* (2016.02)

(58) Field of Classification Search
CPC ................... A61B 90/36; A61B 6/469; A61B 2017/00207; A61B 2017/00199; A61B 34/25; A61B 2090/378; A61B 34/10; A61B 2090/365; G06F 3/013
USPC ........ 715/700, 716, 764, 771, 781, 800, 863
See application file for complete search history.

(56) References Cited

U.S. PATENT DOCUMENTS

| 5,091,926 A * | 2/1992 | Horton et al. ................. 378/114 |
| 5,099,846 A | 3/1992 | Hardy et al. |
| 5,204,625 A * | 4/1993 | Cline et al. .................... 324/306 |
| 5,531,520 A * | 7/1996 | Grimson ................ G01B 11/25 382/131 |
| 5,558,619 A * | 9/1996 | Kami et al. .................... 600/146 |

(Continued)

FOREIGN PATENT DOCUMENTS

| EP | 150726 A1 * | 9/2005 |
| EP | 1 720 039 | 11/2006 |

(Continued)

OTHER PUBLICATIONS

Definition of Anatomy, accessed Feb. 3, 2013, 5 pages.*

(Continued)

*Primary Examiner* — Yongjia Pan
(74) *Attorney, Agent, or Firm* — Tucker Ellis LLP

(57) ABSTRACT

The invention relates to a method for controlling a medical apparatus, wherein: patient image data is generated using an image-generating medical apparatus; a patient image is produced on the basis of this data and displayed on an image output unit; and a medical apparatus is in turn controlled by an interaction with the image.

18 Claims, 1 Drawing Sheet

(56) References Cited

U.S. PATENT DOCUMENTS

| | | | | |
|---|---|---|---|---|
| 5,562,448 | A | * | 10/1996 | Mushabac .......... A61C 13/0004 433/215 |
| 5,769,640 | A | * | 6/1998 | Jacobus ................ B25J 9/1689 434/262 |
| 5,788,688 | A | * | 8/1998 | Bauer et al. ...................... 606/1 |
| 5,867,308 | A | * | 2/1999 | Pensel ................ A61B 3/0025 359/368 |
| 5,886,683 | A | * | 3/1999 | Tognazzini ............ G06F 3/013 345/156 |
| 5,911,036 | A | * | 6/1999 | Wright et al. ................ 700/259 |
| 5,926,264 | A | * | 7/1999 | Beale et al. ................ 356/152.1 |
| 6,016,439 | A | * | 1/2000 | Acker ........................... 600/411 |
| 6,166,544 | A | * | 12/2000 | Debbins et al. ............. 324/309 |
| 6,167,295 | A | * | 12/2000 | Cosman ................ A61B 90/36 600/414 |
| 6,175,610 | B1 | * | 1/2001 | Peter ................................. 378/8 |
| 6,201,984 | B1 | | 3/2001 | Funda et al. |
| 6,317,616 | B1 | * | 11/2001 | Glossop ........................ 600/407 |
| 6,363,134 | B1 | * | 3/2002 | Suzuki ............................ 378/15 |
| 6,405,072 | B1 | * | 6/2002 | Cosman .................... G06T 7/73 600/426 |
| 6,478,425 | B2 | * | 11/2002 | Trajkovic .......... G06K 9/00604 351/209 |
| 6,560,492 | B2 | * | 5/2003 | Borders ........................ 700/17 |
| 6,603,992 | B1 | * | 8/2003 | Debbins et al. ............. 600/420 |
| 6,608,628 | B1 | * | 8/2003 | Ross et al. ................... 345/619 |
| 6,638,223 | B2 | | 10/2003 | Lifshitz et al. |
| 6,665,554 | B1 | * | 12/2003 | Charles et al. .............. 600/427 |
| 6,734,880 | B2 | * | 5/2004 | Chang et al. ................ 715/738 |
| 6,738,656 | B1 | * | 5/2004 | Ferre et al. .................. 600/426 |
| 6,778,846 | B1 | | 8/2004 | Martinez et al. |
| 6,847,336 | B1 | * | 1/2005 | Lemelson et al. ................ 345/8 |
| 6,886,137 | B2 | * | 4/2005 | Peck ..................... G06F 3/0485 345/158 |
| 6,990,170 | B2 | * | 1/2006 | Sugihara et al. ................ 378/15 |
| 7,038,212 | B2 | * | 5/2006 | Wollenweber et al. ....... 250/369 |
| 7,058,901 | B1 | * | 6/2006 | Hafey et al. .................. 715/792 |
| 7,133,137 | B2 | * | 11/2006 | Shimmick ..................... 356/497 |
| 7,176,937 | B2 | * | 2/2007 | Gannon ......................... 345/592 |
| 7,203,277 | B2 | * | 4/2007 | Birkenbach et al. ........ 378/98.5 |
| 7,206,627 | B2 | * | 4/2007 | Abovitz ................ A61B 34/20 345/419 |
| 7,220,000 | B2 | * | 5/2007 | Alster et al. .................. 351/224 |
| 7,227,149 | B2 | * | 6/2007 | Stearns et al. ........... 250/363.03 |
| 7,259,906 | B1 | * | 8/2007 | Islam ............................ 359/334 |
| 7,298,383 | B2 | * | 11/2007 | Vuylsteke ..................... 345/619 |
| 7,313,260 | B2 | * | 12/2007 | Wang et al. .................. 382/128 |
| 7,515,954 | B2 | * | 4/2009 | Harlev et al. ................ 600/509 |
| 7,542,210 | B2 | * | 6/2009 | Chirieleison, Sr. ......................... G02B 27/0093 345/8 |
| 7,561,143 | B1 | * | 7/2009 | Milekic ................... G06F 3/013 345/156 |
| 7,648,461 | B2 | * | 1/2010 | Thiele ........................... 600/453 |
| 7,697,972 | B2 | * | 4/2010 | Verard et al. ................. 600/424 |
| 7,734,331 | B2 | * | 6/2010 | Dhawale et al. ............. 600/431 |
| 7,835,498 | B2 | * | 11/2010 | Bonfiglio et al. ............ 378/115 |
| 7,912,249 | B2 | * | 3/2011 | Mundry ........................ 382/109 |
| 7,965,907 | B2 | * | 6/2011 | Takekoshi .................... 382/305 |
| 8,016,758 | B2 | * | 9/2011 | Wu ................................ 600/440 |
| 8,069,420 | B2 | * | 11/2011 | Plummer ...................... 715/835 |
| 8,190,238 | B2 | * | 5/2012 | Moll et al. ................... 600/424 |
| 8,269,729 | B2 | * | 9/2012 | Han et al. ..................... 345/173 |
| 8,432,465 | B2 | * | 4/2013 | Kramp et al. ............ 348/240.99 |
| 8,520,974 | B2 | * | 8/2013 | Fujita et al. .................. 382/275 |
| 8,527,032 | B2 | * | 9/2013 | Li .................................. 600/424 |
| 8,527,094 | B2 | * | 9/2013 | Kumar et al. ................ 700/259 |
| 2001/0051881 | A1 | * | 12/2001 | Filler ............................ 705/3 |
| 2002/0004729 | A1 | * | 1/2002 | Zak ....................... G06F 19/322 705/3 |
| 2002/0068862 | A1 | * | 6/2002 | Kleiman et al. ............. 600/407 |
| 2002/0087061 | A1 | * | 7/2002 | Lifshitz et al. .............. 600/407 |
| 2002/0105482 | A1 | * | 8/2002 | Lemelson ............... G06F 3/013 345/7 |
| 2002/0109735 | A1 | * | 8/2002 | Chang et al. ................. 345/853 |
| 2002/0113943 | A1 | * | 8/2002 | Trajkovic ........... G06K 9/00604 351/209 |
| 2002/0195565 | A1 | * | 12/2002 | Lecoq ....................... 250/363.03 |
| 2003/0004409 | A1 | * | 1/2003 | Mueller et al. ............... 600/410 |
| 2003/0053061 | A1 | | 3/2003 | Overbeck et al. |
| 2003/0055686 | A1 | * | 3/2003 | Satoh et al. ....................... 705/3 |
| 2003/0093503 | A1 | * | 5/2003 | Yamaki et al. ............... 709/220 |
| 2003/0095144 | A1 | * | 5/2003 | Trevino et al. ............... 345/764 |
| 2003/0095697 | A1 | * | 5/2003 | Wood et al. .................. 382/131 |
| 2004/0030219 | A1 | | 2/2004 | Kim et al. |
| 2004/0106916 | A1 | * | 6/2004 | Quaid et al. ...................... 606/1 |
| 2004/0114034 | A1 | | 6/2004 | Squilla et al. |
| 2004/0212712 | A1 | * | 10/2004 | Stavely .................. A61B 3/113 348/333.03 |
| 2004/0242988 | A1 | * | 12/2004 | Niwa et al. ................... 600/407 |
| 2005/0228256 | A1 | | 10/2005 | Labadie et al. |
| 2005/0267360 | A1 | * | 12/2005 | Birkenbach et al. ......... 600/423 |
| 2006/0025679 | A1 | * | 2/2006 | Viswanathan .......... A61B 34/20 600/424 |
| 2006/0026521 | A1 | | 2/2006 | Hotelling et al. |
| 2006/0030773 | A1 | * | 2/2006 | Uber et al. .................... 600/431 |
| 2006/0100642 | A1 | * | 5/2006 | Yang ...................... A61B 34/70 606/130 |
| 2006/0112334 | A1 | * | 5/2006 | Endrikhovski et al. ....... 715/700 |
| 2006/0262968 | A1 | * | 11/2006 | Drobnitzky ................... 382/128 |
| 2006/0281971 | A1 | * | 12/2006 | Sauer ..................... A61B 34/20 600/109 |
| 2007/0049815 | A1 | * | 3/2007 | Sanjay-Gopal et al. ....... 600/407 |
| 2007/0150841 | A1 | * | 6/2007 | Haras et al. .................. 715/854 |
| 2007/0226646 | A1 | * | 9/2007 | Nagiyama et al. ........... 715/784 |
| 2007/0297663 | A1 | * | 12/2007 | Mundry ........................ 382/131 |
| 2008/0021288 | A1 | * | 1/2008 | Bowman ............... G06F 19/322 600/300 |
| 2008/0021741 | A1 | * | 1/2008 | Holla et al. ....................... 705/3 |
| 2008/0025461 | A1 | * | 1/2008 | Foland et al. .................. 378/17 |
| 2008/0072151 | A1 | | 3/2008 | Song et al. |
| 2008/0086051 | A1 | * | 4/2008 | Voegele ........................ 600/424 |
| 2008/0168403 | A1 | * | 7/2008 | Westerman et al. .......... 715/863 |
| 2008/0183074 | A1 | * | 7/2008 | Carls et al. ................... 600/429 |
| 2008/0253519 | A1 | * | 10/2008 | Bonfiglio et al. .............. 378/65 |
| 2009/0037840 | A1 | * | 2/2009 | Chen ............................. 715/784 |
| 2009/0097723 | A1 | * | 4/2009 | Washburn et al. ............ 382/128 |
| 2009/0125147 | A1 | * | 5/2009 | Wang et al. .................. 700/264 |
| 2009/0131793 | A1 | * | 5/2009 | Stonefield et al. ............ 600/443 |
| 2009/0138800 | A1 | * | 5/2009 | Anderson et al. ............ 715/702 |
| 2009/0146950 | A1 | * | 6/2009 | Maringelli .................... 345/158 |
| 2010/0050110 | A1 | * | 2/2010 | Hughes et al. ............... 715/781 |
| 2010/0123831 | A1 | * | 5/2010 | Crucs ............................ 348/715 |
| 2010/0231504 | A1 | * | 9/2010 | Bloem .................... G06F 3/013 345/156 |
| 2011/0214087 | A1 | * | 9/2011 | Nagiyama et al. ........... 715/784 |
| 2011/0282188 | A1 | * | 11/2011 | Burnside et al. ............. 600/424 |
| 2012/0059249 | A1 | * | 3/2012 | Verard et al. ................. 600/424 |
| 2012/0109150 | A1 | * | 5/2012 | Quaid et al. .................. 606/130 |

FOREIGN PATENT DOCUMENTS

| | | | |
|---|---|---|---|
| JP | 4047567 B2 | * | 2/2008 |
| WO | WO2000051080 A1 | * | 8/2000 |
| WO | 2006/040697 A1 | | 4/2006 |
| WO | 2007/017642 | | 2/2007 |

OTHER PUBLICATIONS

Gesture Definition, accessed Nov. 6, 2013, 1 page.*
Brian S. Tani, Rafael S. Maia, Aldo von Wangenheim, A Gesture Interface for Radiological Workstations, 2007, 6 pages.*
Heiko Drewes, Albrecht Schmidt, Interacting with the Computer Using Gaze Gestures, Sep. 2007, 9 pages (Year: 2007).*
CT and CT aniography, Apr. 13, 2007, 1 page (Year: 2007).*
George P Mylonas, Ara Darzi, Guang Zhong Yang, Gaze-contingent Control for Minimally Invasive Robotic Surgery, 2006, 1 page (Year: 2006).*
European Search Report for corresponding application No. EP 08 15 4245 dated Oct. 6, 2008.

(56) References Cited

OTHER PUBLICATIONS

European Communication for corresponding application No. EP 08 154 245 dated Nov. 12, 2009.
Jun Rekimoto, "SmartSkin: An Infrastructure for Freehand Manipulation on Interactive Surfaces", CHI 2002 Conference Proceedings, Conference on Human Factors in Computing Systems Conference, Minneapolis, MN, Apr. 2002, pp. 113-120.

* cited by examiner

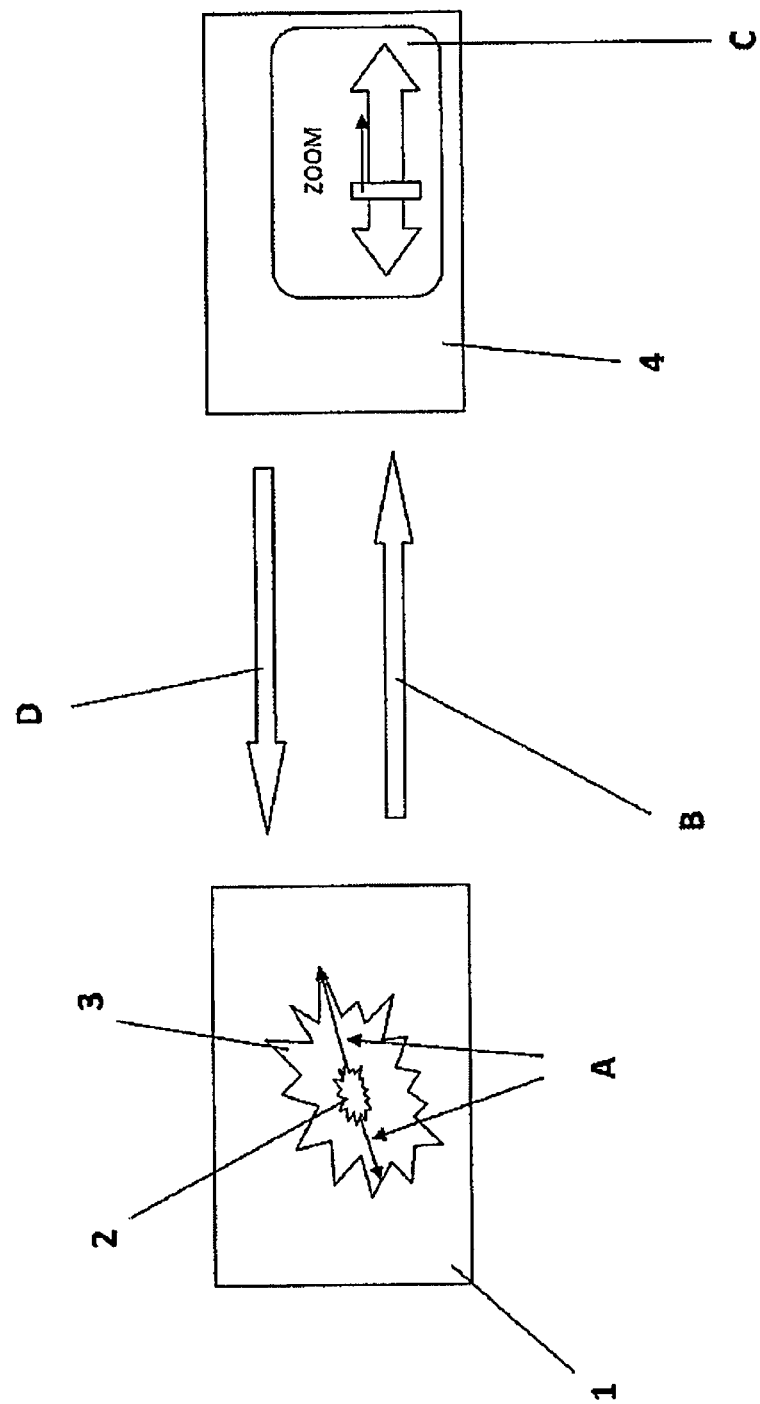

IMAGE-BASED CONTROLLING METHOD FOR MEDICAL APPARATUSES

RELATED APPLICATION DATA

This application claims the priority of U.S. Provisional Application No. 61/045,313, filed on Apr. 16, 2008, which is hereby incorporated in its entirety by reference.

FIELD OF THE INVENTION

The invention relates to an image-based controlling method for medical apparatuses. In particular, image-generating medical apparatuses such as for example endoscopes, CT apparatuses, MR apparatuses, ultrasound apparatuses or video apparatuses are controlled within the framework of the invention.

BACKGROUND OF THE INVENTION

Currently, medical image-generating apparatuses are provided with a range of input apparatuses, such as for example buttons, joysticks, switches and software user-interface elements, and parameters for the image-generating apparatuses are input via software using user interfaces such as for example text input fields, scroll bars and the like.

Other apparatuses are controlled by operator interaction, such as for example when a person carrying out a treatment holds an ultrasound head and positions it at various points on a patient's body. An endoscope system is known from U.S. Pat. No. 5,558,619 which includes automatic control in accordance with the movement of an operator. A method and system for guiding a medical apparatus within a patient using image data is known from U.S. Pat. No. 6,778,846 B1.

SUMMARY OF THE INVENTION

It is the object of the present invention to optimize the control of medical apparatuses, in particular medical imaging apparatuses. The intention is in particular to make control more direct and better adjusted to the user's requirements.

This object is solved in accordance with the invention by a method for controlling a medical apparatus, wherein: patient image data is generated using an image-generating medical apparatus; a patient image is produced on the basis of this data and displayed on an image output unit; and a medical apparatus is in turn controlled by an interaction with the image. The sub-claims define preferred embodiments of the invention.

In the method in accordance with the invention, patient image data is generated using an image-generating medical apparatus, and a patient image is produced on the basis of this data. This image is then displayed on an image output unit. An interaction with the image is then in turn performed, which controls a medical apparatus, for example the image-generating apparatus or another image-generating apparatus (image generation).

In other words, the invention closes a previously open cycle between generating the image, displaying the image and viewing the image, by enabling interaction with the image and then in turn applying the result of this interaction back onto the image-generating apparatus, i.e. onto image production. Thus, the invention uses the images generated in order to in turn control image generation. It enables this by omitting input apparatuses (indirect input apparatuses) such as buttons, joysticks, switches and software interfaces and nonetheless activating desired changes in image representation. Thus, the operator merely has to manipulate the image in order to arrive at the desired new image. This advantageously enables a more direct way of interacting with the medical apparatuses, and desired images or views can be generated in a simple way. It is also possible to provide the user with a simple and very intuitive access to important functions, and it is for example possible to leave the operating details of mechanical devices completely hidden from the user, which significantly simplifies image generation.

The apparatuses can be controlled without contact by an interaction at the image output unit, in particular using touch inputs, multi-touch inputs or gesture inputs (gesture recognition) in front of the image output unit. Another way is by vision detection and/or eye movement detection, wherein it is possible to switch the image output unit on or off, depending on whether a viewer is looking at the patient image or not. The image can also be altered (for example increased in size, brightness or contrast) at the point which is currently being viewed.

In principle, the image data can be influenced in various ways using the apparatus control in accordance with the invention. It is possible to generate new images, retrieve new images from a memory and/or alter the image data using the apparatus control, wherein regenerating often involves a change to the image recording parameters and a new image recording procedure. When retrieving new data, this can be provided in the form of a patient data set, in situ or on a network, and the patient data can for example be changed as a response to inputs by a physician who makes planning inputs (markings, operation instructions, etc.) via the image output.

Within the framework of the invention, it is possible to alter an image recording parameter at the image-generating apparatus using the apparatus control, wherein in particular one or more of the following manipulations is/are performed:
  changing the position of the apparatus or of its image detection element;
  changing the image detection resolution;
  changing the image detection angle;
  changing or shifting the image detection range;
  changing contrast or brightness settings;
  changing the penetration depth;
  changing the layer detection depth.

A number of specific embodiments of the method in accordance with the invention are conceivable, in which one or more of the following actions is/are performed within the framework of image-based apparatus control:
  the image recording characteristics of an endoscope are altered;
  reconstructed images obtained from imaging data sets (CT, MR) are added to or superimposed onto the patient image, or the patient image is at least partially replaced with them;
  the image recording parameters of a medical imaging apparatus (CT, MR, PET, etc.) are altered, and a new image is detected using the changed parameters;
  the sound penetration parameters or position of an ultrasound probe are altered;
  the image recording characteristics of a microscope are altered;
  image-enhancing substances, in particular contrast agents, are administered to the patient;
  ECG or pacemaker parameters are altered;

the room lighting or operation light is altered, in particular concentrated on a location displayed on the patient image;

by manipulating—in particular shifting—its image, an instrument which appears in the image and can be automatically manipulated is correspondingly manipulated—in particular shifted—in reality;

the radiation parameters and/or image recording characteristics of a LINAC are altered;

areas marked in the image are localized and in particular then projected onto the patient.

Again speaking very generally, the method in accordance with the invention can be performed such that the new or altered image data is used to renew, alter or supplement the patient image on the image output unit.

The invention also relates to a program which, when it is running on a computer or is loaded onto a computer, causes the computer to perform a method such as has been described above in various embodiments. It also relates to a computer program storage medium which comprises such a program.

BRIEF DESCRIPTION OF THE DRAWING

The invention is described in more detail below on the basis of a number of embodiments. It can include any of the features described here, individually and in any expedient combination, and can also be interpreted as a device invention if the described or necessary apparatuses are assembled in such a way that a method as described here is implemented. The one enclosed FIGURE schematically shows a control cycle in accordance with the invention, on the basis of a zoom adjustment.

DETAILED DESCRIPTION

The enclosed FIGURE schematically shows an image display unit 1 which, in the present case, is a touch screen monitor, adjacently to the right of which an image-generating apparatus 4, which again is only schematically shown, is also shown in the FIGURE. The reference signs 2 and 3 schematically show images before and after a change, and the letters A, B, C and D illustrate the steps of the method sequence.

A general method sequence in accordance with the present invention would then be the following: the image output 1 initially shows only the image 2—for example, a part of a patient's body—which is or has been recorded with the aid of the image recording apparatus 4; the image recording can be displayed on the basis of new or stored images.

If an operator then wishes to view the object 2 at a greater resolution or size, he goes to the screen 1, which comprises a multi-touch surface. He "grabs" the image 2 at two points and then draws it apart in accordance with the arrows A, such that it acquires the size of the image 3.

This input on the screen 1 is relayed, as apparatus control information, to the image-generating apparatus 4, as shown by the arrow B, wherein the zoom movement (A) can be converted into an apparatus control command directly on the screen by a graphic processing unit, or only later at the medical image recording apparatus.

In the present case, it is shown that the information B concerning the zoom-in arrives at the image-generating apparatus 4, where it is converted into a zoom command which is shown schematically by the box C. This zoom command then generates a change in the image recording parameters of the apparatus 4. For example, the recording element (an image detection element such as a camera, lens, etc.) is moved nearer to the object, or the resolution is increased.

The new image data generated using the altered recording parameters is then transmitted back to the monitor 1, as shown by the arrow D, and the image 3 is then displayed on said monitor 1 at the improved resolution and in its enlarged form. Thus, the control cycle is closed, and the operator is provided with a new image, without having to manipulate the apparatus 4 himself.

Various embodiments of the invention shall now be discussed in more detail below:

Endoscope: the image-generating medical apparatus can be an endoscope. An endoscope generally has a rigid or flexible tube which, when introduced into a patient, sends back an image (through the tube). In accordance with the invention, gestures performed on the image are used to modify the position and/or other parameters of the endoscope. In this case, and more generally, such gestures can in the sense of the invention be gestures which are performed by touching a touch-sensitive monitor (touch screen), or gestures which are identified by gesture recognition systems and which do not necessarily require touching a monitor or image output apparatus. In the present case, gesture recognition can for example cause the tip of the endoscope tube to be moved forwards (zoom-in) or backwards (zoom-out). Such a movement can be mechanically assisted, wherein the control commands then act on this mechanism. It is also possible to alter the viewing direction of the endoscope, for example by performing a shifting gesture on the image, by which the tip of the endoscope can be shifted in any direction. A rotation of the endoscope can for example be triggered by a rotating control movement. Other gestures could be used to increase or reduce the light intensity, change the lens of the endoscope, or perform any other action which is possible using the endoscope hardware.

Reconstructed image (instead of or in addition to the endoscope image): when controlling an endoscope (or also when controlling other imaging apparatuses), it is possible using the invention to extend imaging by superimposing the generated image (endoscope image) with an image which is reconstructed from magnetic resonance or computer tomography data, wherein it can be fluidly superimposed in a transition to desired portions, or the region being viewed by the apparatus (endoscope) can also be completely replaced with an MR or CT reconstruction, if for example an endoscope image is not available or the endoscope cannot physically be moved to the position at which the image is to be produced.

MR/CT: in this case, an image which is to be viewed by a user is generated using a tomographic scan, such as for example MR (magnetic resonance tomography), CT (computer tomography) or PET (positron emission tomography) or any other device which generates multilayered scans. In accordance with the invention, the gestures performed on the image then modify the scan characteristics of the image-generating apparatus. The user can for example define an area of interest in the image, and the image-generating apparatus then performs a more detailed re-scan of the area of interest. One gesture can for example be used to alter the tomograph detection distance during such a re-scanning procedure, so as to increase the precision. In another conceivable application, a user navigation input which exceeds/overextends the current boundaries of the data set causes images to be re-acquired, wherein it may be advantageous for the patient to remain on the scanner table while the first images are evaluated.

Ultrasound: in order to control ultrasound image acquisition, gestures on an ultrasound image by the user can for example alter the penetration depth of the image (zoom image). In the case of TEE (trans-esophageal echocardiogram) ultrasound detection, the ultrasound probe is arranged in the patient's esophagus and rotated in order to acquire multiple tomographs. In the case of this recording, a scroll gesture on the images can for example be used to alter the rotation of the probe and so display different layers. A shifting gesture on the images is for example used to move the ultrasound probe upwards or downwards in the esophagus.

Microscope: when using a medical microscope (pathological microscope), any zoom gestures or shifting gestures on the images can be converted into movements of the microscope lenses and/or the position of the microscope. For the user, this creates the impression that he is "navigating" through a set of images.

Acquisition parameters: in the prior art, the user can only change the brightness and contrast of images after they have been acquired, whereas in accordance with the invention, user gestures on the image can alter the brightness and contrast in the area which is provided by the image or also in an area influenced by the acquisition parameters of the apparatus. This enables the apparatus to be used to improve image acquisition for exactly those settings which the user has chosen. In an extension of this concept, it is possible to define gestures which can in turn change any acquisition parameters of the apparatus.

Contrast agent: in this case, image manipulation can be used to trigger the administering of a contrast agent. For example, the user would perform a gesture which incorporates the command for viewing the image with contrast, and if no such image is available, this request automatically causes a contrast agent to be injected, in order to be able to generate such an image.

ECG: ECG curves show electrical cardiac activity. Interactive images, which display an ECG trace, can be manipulated. Modifications to the ECG curve, for example quickening or slowing the pulse, are interpreted by another device which takes steps to change the current ECG to the desired ECG (for example, administering dobutamine in order to quicken the pulse).

Pacemakers: In an extension of the concept of regulating the pulse, it is possible to use an ECG curve to modify the parameters of a pacemaker or implantable cardioverter defibrillator. These devices are fine-tuned for each patient, and the heart rate is changed by changing the apparatus parameters. In accordance with the present invention, the user can directly change the ECG curve (ECG diagram), and this modification is then converted into changed parameters for the pacemaker or defibrillator. In this way, such apparatuses can be more quickly and easily fine-tuned. This case also shows that within the framework of the present invention, the displayed images do not necessarily have to be images of actual objects, but can also be images such as diagrams which represent physical functions. These images are also referred to in the present case as "patient images".

Operating room lighting: in this embodiment, an image display device can be used to control another apparatus which does not necessarily generate an image itself but which assists image generation. By selecting a point on an image at the image output unit, the lights in the operating room are automatically rotated into a position in which they concentrate their light on the chosen point. This is advantageously performed after the patient and the acquired images have been registered in a navigation/tracking system.

If, in accordance with this embodiment, the illuminated point becomes brighter, it may be possible to take a better or more precise video image which can then likewise be displayed on the image output unit, on its own or in addition to the previous image. Thus, within the framework of the invention, the imaging apparatus controlled by manipulating can be the same as the imaging apparatus which took the first image (the manipulated image) or can be another imaging apparatus which generates additional image data.

Controlling an apparatus in the image: in this embodiment variant, an image is used to control a device which is displayed on the image. One example is when an intra-operative image shows the position of a biopsy needle. By moving the needle in the image (using input gestures), the actual physical object is automatically moved, which enables exact positioning.

LINAC: in order to control a linear accelerator (radiotherapy), this variation of the invention uses gestures which manipulate the image, to select and alter beams and/or beam shapes. Together with an image produced during the procedure, this is used to correct and shift the beams (interaction with intra-procedural images).

Regions or images marked on the patient: in this case, any region (two-dimensional or three-dimensional) can be marked in a medical image. If the position of the patient has been registered relative to the image data, it is then for example possible to project the exact position of the region—marked in the image output—onto the patient, for example using a laser.

Modifying accessories/other apparatuses: in accordance with this variation, non-medical images are output and objects in them are manipulated. One example is to display an image of an operating theatre, wherein by manipulating the image with the aid of gestures, it is for example possible to change the position or inclination of a table. Another example is a dashboard software for operating room planning, in which the software images show all the operating rooms and their current status. Using gestures on the doors and lifts, it is then possible to change their position. One example is to open all the doors to the rooms which are accessible from one hallway.

Visual control: in accordance with this embodiment, non-tactile interaction with the systems is used, such as has already been described above. Visual controls are used instead of touching monitors or gesture recognition, in order to interact with the images. A device which is suitable for this purpose recognizes eye movements, for example, and automatically sets the image display in accordance with the focus of view. In one example, the parameters of a medical image detection apparatus are changed for or in accordance with the area of the image which the user is currently looking at. Another example is to extend scan detection when the user directs his view towards the boundaries of the scan image material provided.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electromagnetic, infrared or semiconductor system, apparatus, device or medium of propagation such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

Although the invention has been shown and described with respect to one or more particular preferred embodiments, it is clear that equivalent amendments or modifications will occur to the person skilled in the art when reading and interpreting the text and enclosed drawings of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment or embodiments illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for controlling a medical imaging apparatus by using a computer, comprising:
    using an image-generating medical imaging apparatus configured to capture image data corresponding to a tomographic scan of a patient;
    producing a patient image based on the generated image data and displaying the patient image on an image output unit, said patient image comprising an anatomical representation of the patient;
    controlling the medical imaging apparatus based on an interaction with the patient image, said controlling comprising altering at least one image acquisition parameter usable for controlling the medical imaging apparatus to capture new image data corresponding to a new tomographic scan of the patient, and said interaction comprising:
        using multi-touch inputs which are executed by touching the anatomical representation of the patient on the image output unit simultaneously at different positions, and
        vision detection and/or eye movement detection based on how a viewer looks at the patient image;
    changing the image at the point being viewed by partially replacing the patient image with reconstructed images based on the new image data; and
    switching the image output unit on or off based on how the viewer looks at the patient image,
    wherein generating image data corresponding to the patient includes generating a multi-layered patient scan, further comprising generating a new multi-layered patient scan based on the altered parameters;
    evaluating whether the altered parameters exceed boundaries of a patient data set, which causes image data to be re-captured.

2. The method according to claim 1, wherein controlling the medical imaging apparatus includes controlling an image-generating apparatus.

3. The method according to claim 1, wherein controlling the medical imaging apparatus includes controlling the medical apparatus by interaction at the image output unit.

4. The method according to claim 3, wherein controlling based on an interaction includes using gesture inputs/recognition to interact with the image.

5. The method according to claim 1, wherein controlling the medical imaging apparatus includes controlling the medical apparatus by manipulating the image.

6. The method according to claim 5, wherein manipulating the image includes increasing/decreasing the size of the image, rotating the image or shifting a viewing plane.

7. The method according to claim 1, wherein controlling the medical imaging apparatus includes generating new image data based on control commands generated by interacting with the image.

8. The method according to claim 7, further comprising using the new image data to renew, alter or supplement the patient image on the image output unit.

9. The method according to claim 1, further comprising retrieving new image data from a memory based on control commands generated by interacting with the image.

10. The method according to claim 1, wherein controlling the medical imaging apparatus includes altering an image recording parameter at the image-generating apparatus based on control commands generated by interacting with the image.

11. The method according to claim 10, wherein altering at least one image acquisition parameter includes at least one of:
    changing the position of the apparatus or of its image detection element;
    changing the image detection resolution;
    changing the image detection angle;
    changing or shifting the image detection range;
    changing the penetration depth; or
    changing the layer detection depth.

12. The method according to claim 1, further comprising configuring operation of the medical imaging apparatus, said configuring including at least one of:
    adding or superimposing reconstructed images obtained from imaging data sets (CT, MR) onto the patient image;
    administering image-enhancing substances to the patient;
    altering ECG or pacemaker parameters;
    manipulating an instrument by manipulating an image of the instrument; or
    localizing areas marked in the image.

13. The method according to claim 12, wherein manipulating the instrument or the instrument image comprises shifting the instrument or the instrument image.

14. The method according to claim 12, wherein localizing areas includes projecting the localized areas onto the patient.

15. A computer program embodied on a non-transitory computer readable medium, comprising computer executable instructions configured to perform the method in accordance with claim 1.

16. The method according to claim 1, wherein altering at least one image acquisition parameter includes at least one of:
- altering image recording characteristics of an endoscope;
- detecting a new image using the altered image acquisition parameters;
- altering sound penetration parameters or a position of an ultrasound probe;
- altering image recording characteristics of a microscope;
- altering room lighting or operation light;
- altering radiation parameters and/or image recording characteristics of a LINAC.

17. The method according to claim 16, wherein altering the room lighting or operation light includes concentrating the room lighting or operation light on a location displayed on the patient image.

18. A method for controlling a medical imaging apparatus by using a computer, comprising:
- using an image-generating medical imaging apparatus configured to capture image data corresponding to a tomographic scan of a patient;
- producing a patient image based on the generated image data and displaying the patient image on an image output unit, said patient image comprising an anatomical representation of the patient;
- controlling the medical imaging apparatus based on an interaction with the patient image, said controlling comprising altering at least one image acquisition parameter usable for controlling the medical imaging apparatus to capture new image data corresponding to a new tomographic scan of the patient, and said interaction comprising vision detection and/or eye movement detection based on how a viewer looks at the patient image;
- changing the image at the point being viewed by partially replacing the patient image with reconstructed images based on the new image data;
- switching the image output unit on or off based on how the viewer looks at the patient image; and
- evaluating whether the altered parameters exceed boundaries of a patient data set, which causes image data to be re-captured.

* * * * *